(12) United States Patent
Dolitzky et al.

(10) Patent No.: US 7,332,612 B2
(45) Date of Patent: Feb. 19, 2008

(54) AMORPHOUS AND CRYSTALLINE FORMS OF LOSARTAN POTASSIUM AND PROCESS FOR THEIR PREPARATION

(75) Inventors: Ben Zion Dolitzky, Petach Tiqva (IL); Shlomit Wizel, Petah Tikva (IL); Gennady Nisnevich, Haifa (IL); Igor Rukhman, Technion (IL); Julia Kaftanov, Haifa (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/293,820

(22) Filed: Nov. 13, 2002

(65) Prior Publication Data

US 2004/0006237 A1    Jan. 8, 2004

Related U.S. Application Data

(60) Provisional application No. 60/401,278, filed on Aug. 5, 2002, provisional application No. 60/333,034, filed on Nov. 14, 2001.

(51) Int. Cl.
   *C07D 403/10*    (2006.01)
(52) U.S. Cl. ..................... 548/250; 548/252
(58) Field of Classification Search ............... 548/250, 548/252
   See application file for complete search history.

(56) References Cited

U.S. PATENT DOCUMENTS

| | | |
|---|---|---|
| 5,128,355 A | 7/1992 | Carini et al. |
| 5,130,439 A | 7/1992 | Lo et al. |
| 5,138,069 A | 8/1992 | Carini et al. |
| 5,140,037 A | 8/1992 | Chiu et al. |
| 5,155,118 A | 10/1992 | Carini et al. |
| 5,206,374 A | 4/1993 | Lo |
| 5,310,928 A | 5/1994 | Lo et al. |
| 5,608,075 A | 3/1997 | Campbell, Jr. et al. |
| 5,663,186 A | 9/1997 | Nelson et al. |
| 5,663,187 A | 9/1997 | Nelson et al. |
| 5,962,500 A | 10/1999 | Eide et al. |

FOREIGN PATENT DOCUMENTS

WO    WO 95/17396 A    6/1995

OTHER PUBLICATIONS

K. Raghavan, et al. "A Spectroscopic Investigation of Losartan Polymorphs", *Pharmaceutical Research*, vol. 10, No. 6, 1993, pp. 900-904.

*Primary Examiner*—Laura L. Stockton
(74) *Attorney, Agent, or Firm*—Kenyon & Kenyon LLP

(57) ABSTRACT

This invention relates to novel amorphous losartan potassium, novel losartan potassium in a crystalline form that is a hydrate, novel crystalline losartan potassium Form IV and solvates thereof, novel crystalline losartan potassium Form V and solvates thereof, to processes for their preparation, to compositions containing them and to their use in medicine. This invention further relates to a novel process for preparing crystalline losartan potassium Form I and Form II.

10 Claims, 9 Drawing Sheets

AMORPHOUS AND CRYSTALLINE FORMS OF LOSARTAN POTASSIUM AND PROCESS FOR THEIR PREPARATION

CROSS REFERENCE TO RELATED APPLICATIONS

This application claims the benefit of U.S. provisional application Serial No. 60/333,034, filed Nov. 14, 2001, and U.S. provisional application Serial No. 60/401,278, filed Aug. 5, 2002, both of which are incorporated herein by reference.

FIELD OF THE INVENTION

This invention relates to novel amorphous losartan potassium, novel losartan potassium in a crystalline form that is a hydrate, novel crystalline losartan potassium Form IV and solvates thereof, novel crystalline losartan potassium Form V and solvates thereof, to processes for their preparation, to compositions containing them and to their use in medicine. This invention further relates to a novel process for preparing crystalline losartan potassium Form I and Form II.

BACKGROUND OF THE INVENTION

Losartan potassium, also known as 2-butyl-4-chloro-1-[[2'-(1H-tetrazol-5-yl)[1,1'-buphenyl]-4-yl]-1H-imidazole-5-methanol monopotassium salt, is a competitive $AT_1$ angiotensin II receptor antagonist and has the following formula (I):

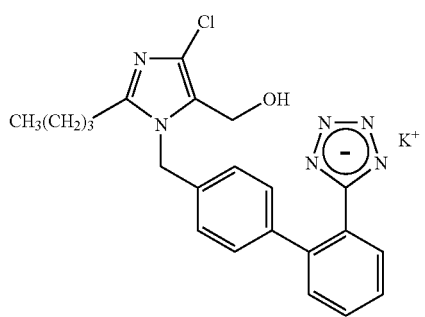

Activation of $AT_1$ receptors in the outer membrane of vascular smooth muscle cells of the heart and arteries causes the tissues to constrict. $AT_1$ receptors are activated by an octa-peptide, angiotensin II. Angiotensin II helps to maintain constant blood pressure despite fluctuations in a person's state of hydration, sodium intake and other physiological variables. Angiotensin II also performs the regulatory tasks of inhibiting excretion of sodium by the kidneys, inhibiting norephedrin reuptake and stimulating aldosterone biosynthesis. By inhibiting angiotensin II binding to $AT_1$ receptors, losartan disrupts the vasoconstriction mediated by $AT_1$ receptors. Blocking vasoconstriction by angiotensin II has been found to be beneficial to patients with hypertension.

In 1995, losartan became the first nonpeptide $AT_1$ antagonist approved by the U.S. Food and Drug Administration for clinical use. In particular, losartan is approved for the treatment of hypertension alone or in combination with other antihypertensive agents. Losartan may be administered orally as its mono-potassium salt. Losartan potassium is available by prescription in tablet form as a sole active ingredient (Cozaar®: Merck) and as a co-active ingredient with hydrochlorothiazide (Hyzaar®: Merck).

U.S. Pat. No. 5,608,075, which is hereby incorporated by reference, discloses distinct crystalline structures, or forms, of losartan potassium which were designated Form I and Form II based on their respective thermal stability. As described in the '075 patent, losartan potassium Form II was prepared by heating Form I crystals in a differential scanning calorimetric (DSC) cell in an open pan to 255° C. at a heating rate of 10° C./minute under a nitrogen atmosphere. The '075 patent indicates that the change in crystal structure was detected as a change in the powder X-ray diffraction (PXRD) pattern. According to the '075 patent, Form II can be converted back into Form I at 25° C. in isopropanol, methyl ethyl ketone or ethyl acetate. Further, according to the '075 patent, Form I is the solid consistently obtained by solvent isolation, including recrystallization. Form II could only be obtained from DSC or related high temperature experiments.

The present invention relates to the solid state physical properties of losartan potassium. These properties can be influenced by controlling the conditions under which losartan potassium is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetric (DSC) and can be used to distinguish some polymorphic forms from others. A particular polymorphic form may also give rise to distinct spectroscopic properties that may be detectable by powder X-ray crystallography, solid state $^{13}C$ NMR spectrometry and infrared spectrometry.

In the '075 patent, losartan potassium Form I is prepared as follows. In one portion, a potassium hydroxide solution is added to losartan. The slurry is aged at room temperature for 30 minutes, during which time most of the solid dissolves. The cloudy solution is filtered and the solids collected on a sintered glass funnel. The pH of the filtrate is measured at 9.05. The aqueous solution is added slowly to a refluxing azeotropic mixture of cyclohexane/isopropanol (69° C.) whereupon the ternary azeotrope cyclohexane/isopropanol/water (64° C.) begins to distill. When the solution is dry, the temperature of the overhead rises to 69° C. and the potassium salt crystallizes. When the water content of the pot is <0.05% the distillation is halted and the white slurry is cooled to room temperature. Polymorph Form I, a white crystalline solid, is collected on a sintered glass funnel and washed with 10-15 ml of cyclohexane/isopropanol 67/33 and dried in a vacuum oven. The same method was used in U.S. Pat. No. 5,962,500 (Ex. 10), U.S. Pat. No. 5,663,187 (Ex. 10), U.S. Pat. No. 5,663,186 (Ex. 10) and U.S. Pat. No. 5,301,928 (Ex. 26, III).

Losartan potassium can be prepared by a variety of methods. For instance, in U.S. Pat. Nos. 5,128,355, 5,138,069 and 5,155,118, Example 316, Part D in all, losartan is isolated as its potassium salt by crystallization from a mixture of isopropyl alcohol and heptane. The crystals were reported to have a melting point above 250° C.

In U.S. Pat. No. 5,962,500, Example 5, and U.S. Pat. Nos. 5,206,374 and 5,310,928, Example 21 in both, losartan potassium salt was generated from a solution of losartan by extracting losartan from the solution with an adsorbent, treating the adsorbent with monobasic potassium phosphate and eluting losartan potassium from the adsorbent with 20% aqueous THF. The eluent was then concentrated and diluted with isopropyl alcohol, which yielded crystalline losartan potassium. According to the '500 patent, the product was also isolated by spray drying.

In U.S. Pat. Nos. 5,130,439, 5,206,374 and 5,310,928, Example 8 in all, losartan potassium salt was crystallized from a mixture of isopropyl alcohol, water and heptane. The product was collected by filtration, rinsed with heptane and dried at 50° C. in a vacuum oven to yield a white solid that decomposed at 267-269° C.

A crystalline form of a substance has well-defined physical properties; however, an amorphous form will exhibit a "smearing" of some of those properties due to the lack of long range structural order. An amorphous substance will produce a near featureless PXRD pattern although the diffraction pattern of a crystalline form of the same substance may have many well-resolved reflections. Generally, molecular interactions caused by tight crystal packing make a substance more thermally stable and less soluble than the substance would be in an amorphous state. Although thermal stability is a desirable characteristic of a pharmaceutical compound, it is often the case that increased, rather than decreased, solubility is desired. The rate of dissolution of an active ingredient in a patient's gastric fluid can have therapeutic consequences since it imposes an upper limit on the rate at which an orally-administered active ingredient can reach the patient's bloodstream. Increased solubility in aqueous fluids, therefore, can increase bioavailability. The effect that the solid-state has on bioavailability may be so significant that a crystalline form of a drug cannot be considered bioequivalent to the amorphous form.

In view of the foregoing, it would be desirable to have losartan potassium with improved bulk handling and dissolution properties.

SUMMARY OF THE INVENTION

In one aspect, the present invention relates to amorphous losartan potassium.

In another aspect, the present invention relates to a process for preparing amorphous losartan potassium, including the steps of dissolving losartan potassium in a solvent to form a solution and lyophilizing the solvent from the solution to afford amorphous losartan potassium.

In another aspect, the present invention relates to a process for preparing amorphous losartan potassium, including the steps of dissolving losartan potassium in water to form a solution and lyophilizing the water from the solution to afford amorphous losartan potassium.

In another aspect, the present invention relates to a process for preparing amorphous losartan potassium, including the steps of dissolving losartan potassium in a solvent to form a solution and distilling the solvent from the solution to afford amorphous losartan potassium.

In another aspect, the present invention relates to a process for preparing amorphous losartan potassium, including the steps of dissolving losartan potassium in methanol to form a solution and distilling the methanol solvent from the solution to afford amorphous losartan potassium.

In another aspect, the present invention relates to a new crystalline form of losartan potassium that is a hydrate. More particularly, the invention relates to a crystalline form of losartan potassium that is a tetrahydrate denoted Form III. The crystalline form of losartan potassium that is a hydrate is characterized by a powder X-ray diffraction pattern with peaks at about 5.7, 8.9, 13.3, 17.5, 20.0, and 21.1±0.2 degrees 2θ. Losartan potassium Form III has a water content of from about 12 to about 16%, and more particularly about 14%.

In another aspect, the present invention relates to a process for preparing losartan potassium in crystalline form that is a hydrate, including the steps of exposing amorphous losartan potassium or losartan potassium Form I to an atmosphere having a relative humidity greater than about 60%. The crystalline form that is a hydrate has at least one characteristic of Form III.

In another aspect, the present invention relates to a new crystalline form of losartan potassium, which is characterized by a powder X-ray diffraction pattern with peaks at about 4.3, 15.6 and 23.4±0.2 degrees 2θ. Another characterization of this novel form is a differential scanning calorimetric thermogram having four endotherms at about 78° C., 218° C., 240° C., and 255° C. Said new crystalline form denoted Form IV and solvates thereof.

In another aspect, the present invention relates to a process for preparing losartan potassium and solvates thereof having at least one characteristic of Form IV, including the steps of providing a solution of losartan potassium in a solvent to form a solution, the solvent being characterized as having a boiling point of about 135° C. or below (e.g. ethanol), adding methylene chloride to the solution whereby a suspension is formed, and isolating losartan potassium Form IV and solvates thereof. Preferably, the solvate is an ethanolate.

In another aspect, the present invention relates to a new crystalline form of losartan potassium, which is characterized by a powder X-ray diffraction pattern with peaks at about 6.4, 12.2, 20.7, 21.5 and 22.5±0.2 degrees 2θ. Said new form denoted Form V and solvates thereof.

In another aspect, the present invention relates to a process for preparing losartan potassium and solvates thereof having at least one of the characteristics of Form V, including the steps of providing a solution of losartan potassium in a solvent to form a solution, the solvent being characterized as having a boiling point of about 135° C. or below (e.g. ethanol), adding hexane to form a mixture, and isolating losartan potassium Form V and solvates thereof. Preferably, the solvate is an ethanolate.

In another aspect, the present invention relates to a process for preparing crystalline losartan potassium Form II, including the steps of providing a solution of losartan potassium in a solvent to form a solution, the solvent being characterized by its capacity to solubilize losartan potassium at room temperature at a concentration up to at least about 0.1 gram per milliliter of solvent and as having a boiling point of about 135° C. or below (e.g. ethanol), adding the solution to xylene to form a mixture, evaporating the solvent from the mixture, and isolating losartan potassium Form II therefrom.

In yet another aspect, the present invention relates to a process for preparing crystalline losartan potassium Form I by isolation from a solvent, including the steps of providing a solution of losartan potassium in a first solvent to form a solution, the solvent being characterized as having a boiling point of about 135° C. or below (e.g. ethanol and isopropyl alcohol), reducing the temperature of the solution, optionally adding a second solvent selected from the group consisting of ethyl acetate, toluene, acetone, methyl ethyl ketone, methylene chloride, acetonitrile, dimethyl carbonate, and hexane to form a mixture, and isolating losartan potassium Form I therefrom.

In still another aspect, the present invention relates to a process for preparing crystalline losartan potassium Form I including the step of heating losartan potassium Form III. Preferably, losartan potassium Form III is heated to a temperature of at least about 50° C., and more preferably about 100° C.

DETAILED DESCRIPTION OF THE INVENTION

As used herein, the phrase "losartan potassium Form 'P'," where P is a Roman numeral, refers to a crystalline form of losartan potassium that one of skill in the art can identify as a distinct entity distinguishable from other crystalline forms of losartan potassium based on the characterization provided herein. As used herein, the phrase having "at least one characteristic of Form 'P'," where P is a Roman numeral, refers to a crystalline form of losartan potassium that possesses one of the PXRD peaks or endotherms of a DSC thermogram provided herein. For example, a single or a combination of PXRD peaks which is not found in another crystalline form of losartan potassium is enough to show at least one of the characteristics of Form P. A single or a combination of endotherms of a DSC thermogram may also serve the same purpose.

In one embodiment, this invention provides novel amorphous losartan potassium. "Amorphous" means a solid without long range crystalline order. Amorphous losartan potassium in accordance with the invention preferably contains less than about 10% crystalline losartan potassium, and more preferably is essentially free of crystalline losartan potassium. "Essentially free of crystalline losartan potassium" means that no crystalline losartan potassium can be detected within the limits of a powder X-ray diffractometer comparable to the instrumentation described below in the Examples section.

Figure 1:
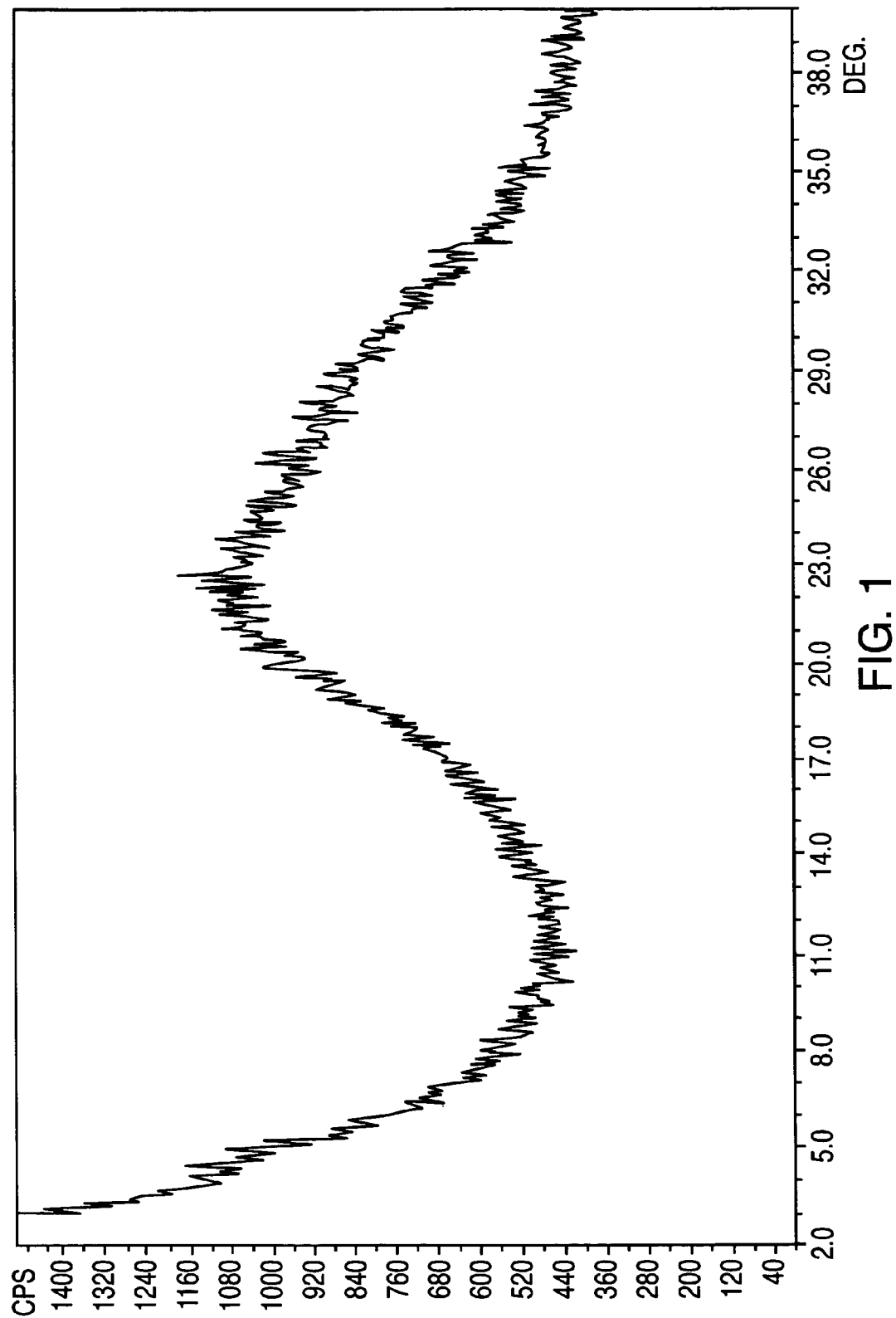
FIG. 1 is a PXRD pattern for amorphous losartan potassium produced by lyophilization of an aqueous solution.
Figure 2:
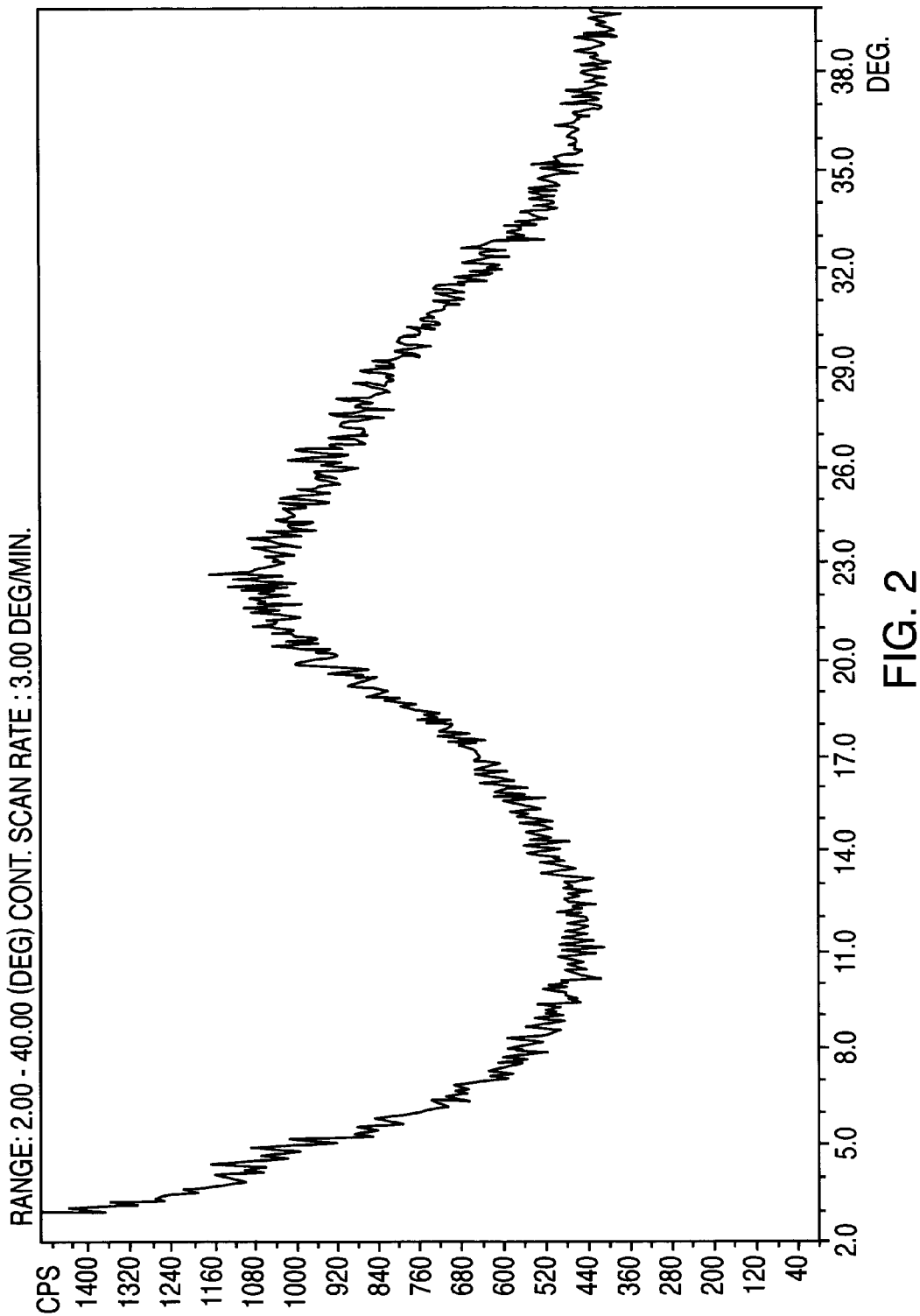
FIG. 2 is a PXRD for amorphous losartan potassium produced by distillation of an aqueous solution.
Figure 3:
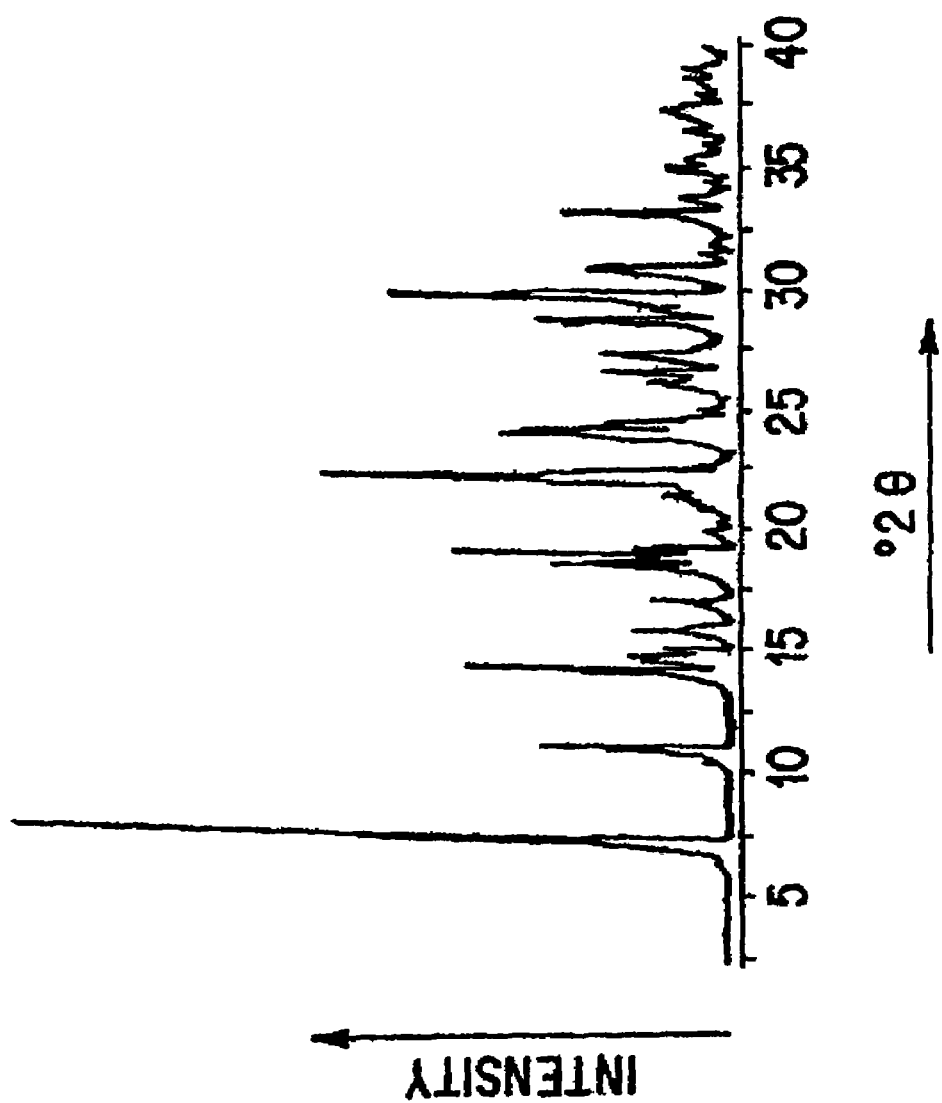
FIG. 3 reprises FIG. 2(A) of U.S. Pat. No. 5,608,075 and is a PXRD pattern for crystalline Form I losartan potassium.

The amorphous character and purity of the material we have produced is confirmed by PXRD patterns obtained from samples thereof, which are provided as FIGS. 1 and 2. Both patterns are without intense focused reflections and are featureless, but for a halo with a maximum centered at about 22 degrees 2θ. For comparison, a diffraction pattern of crystalline Form I losartan potassium prepared following procedures described in U.S. Pat. No. 5,608,075 is provided as FIG. 3.

In another embodiment, the present invention provides processes for making amorphous losartan potassium by either a lyophilization process or a distillation process. The starting material for either process can be losartan potassium obtained by any method, such as the methods described in the patents previously discussed, i.e., U.S. Pat. Nos. 5,128,355; 5,130,439; 5,138,069; 5,155,118; 5,206,374; 5,310,928; 5,608,075; 5,663,187; 5,663,186 and 5,962,500.

In one embodiment, the present invention provides a lyophilizing (freeze drying) process for preparing amorphous losartan potassium, including the steps of dissolving losartan potassium in a solvent to form a solution and lyophilizing the solvent from the solution to afford amorphous losartan potassium.

In a first step of the lyophilization process, losartan potassium is preferably dissolved in an aqueous (prepared with water) solvent, more preferably dissolved in an alcohol solvent, and most preferably dissolved in water to form a solution. In particular, losartan potassium is highly soluble in water, allowing the complete dissolution of losartan potassium at room temperature at a concentration of 0.5 g $ml^{-1}$ and higher. The use of a highly concentrated solution, e.g. from about 0.25 g $ml^{-1}$ to about 1 g $ml^{-1}$ is therefore preferred.

In a second and preferred step of the lyophilization process, a solution of losartan sodium in a solvent is lyophilized to leave a solid residue containing losartan potassium in an amorphous state. In this invention, the lyophilization step is performed in two stages: freezing and drying.

In the first stage of lyophilization, the temperature of the solution is reduced until the solution is completely frozen, typically to temperatures as low as minus 50° C., and below, to produce a frozen mixture. Such cooling causes the solute and solvent to separate into separate solid phases. Generally, phase separation will yield a solute in a crystalline, microcrystalline or amorphous state. Preferably in this invention, cooling is performed rapidly to inhibit formation of solute crystals. More preferably, the solution is cooled using liquid nitrogen with swirling of the vessel containing the solution to coat the wall of the vessel and accelerate freezing. Once the solution has been completely frozen, it is then possible to remove the separated solvent from the frozen mixture by heating the contents slowly so that the solvent leaves the frozen mixture through sublimation.

The drying stage is preferably conducted under vacuum so that the frozen solvent will vaporize without melting. Heat is applied to transform the frozen solvent into solvent vapor. This vapor migrates through the frozen mixture and escapes into the evacuated space outside of the frozen mixture. The vapor is re-condensed on a refrigerated surface, or condenser, that is in fluid communication with the frozen mixture. The vapor pressure of the solvent above the frozen mixture is low. Fluid communication is typically through large diameter pipes to facilitate random migration of the chilled vapor to the condenser. The condenser is maintained at a temperature below that of the frozen mixture to drive the drying process.

When the solvent is water, typical lyophilization conditions for producing amorphous losartan potassium include where the temperature of the frozen mixture is from about −50° C. to about 0° C. before vacuum is applied. The vacuum is typically about 0.05 mm Hg or less, more preferably about 0.01 mm Hg or less and the temperature of the frozen mixture is from about −50° C. to about 20° C. during the drying stage. The drying time using these conditions and standard equipment is from about 24 hours to about 96 hours for about a 250 g sample of losartan potassium. These conditions were optimized using an Edwards lyophilizer.

In another embodiment, the present invention also provides a distillation process for preparing amorphous losartan potassium, including the steps of dissolving losartan potassium in a solvent to form a solution and distilling the solvent from the solution to dryness to afford amorphous losartan potassium.

In a first step of the distillation process, losartan potassium is preferably dissolved in an aqueous solvent, more preferably dissolved in an alcohol solvent, and most preferably dissolved in methanol to form a solution. In particular, losartan potassium is highly soluble in methanol, allowing the complete dissolution of losartan potassium at room temperature.

In a second step of the distillation process, using conventional distillation methods, the solvent is removed from the solution to dryness, thereby leaving a solid residue containing amorphous losartan potassium.

The distillation process can be preformed at atmospheric pressure or reduced pressure. Preferably the solvent is removed at a pressure of about 760 mm Hg or less, more preferably at about 300 mm Hg or less, more preferably at about 100 mm Hg or less, and most preferably from about 20 to about 100 mm Hg.

Figure 4:
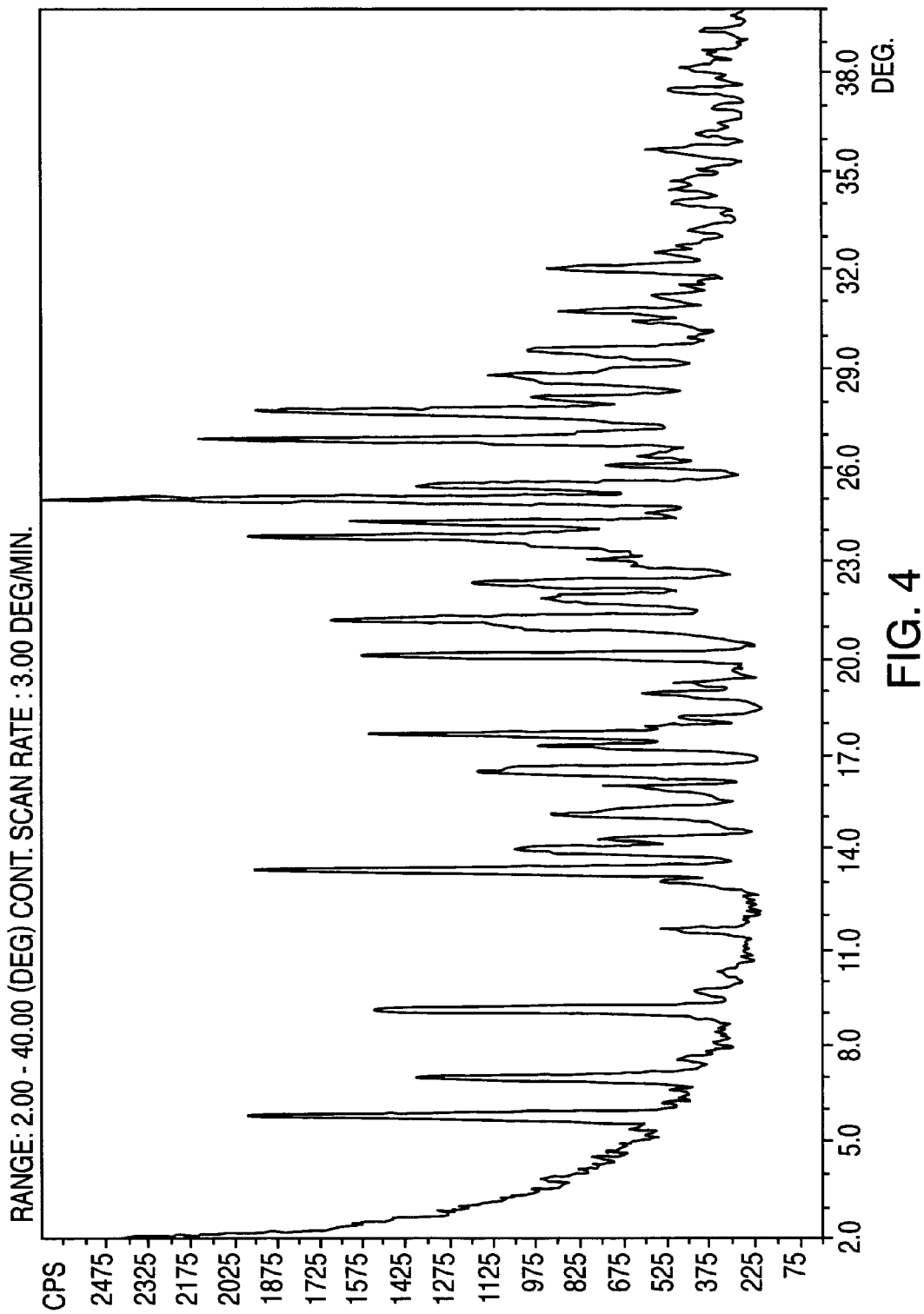
FIG. 4 is a PXRD pattern for losartan potassium Form III.
Figure 5:
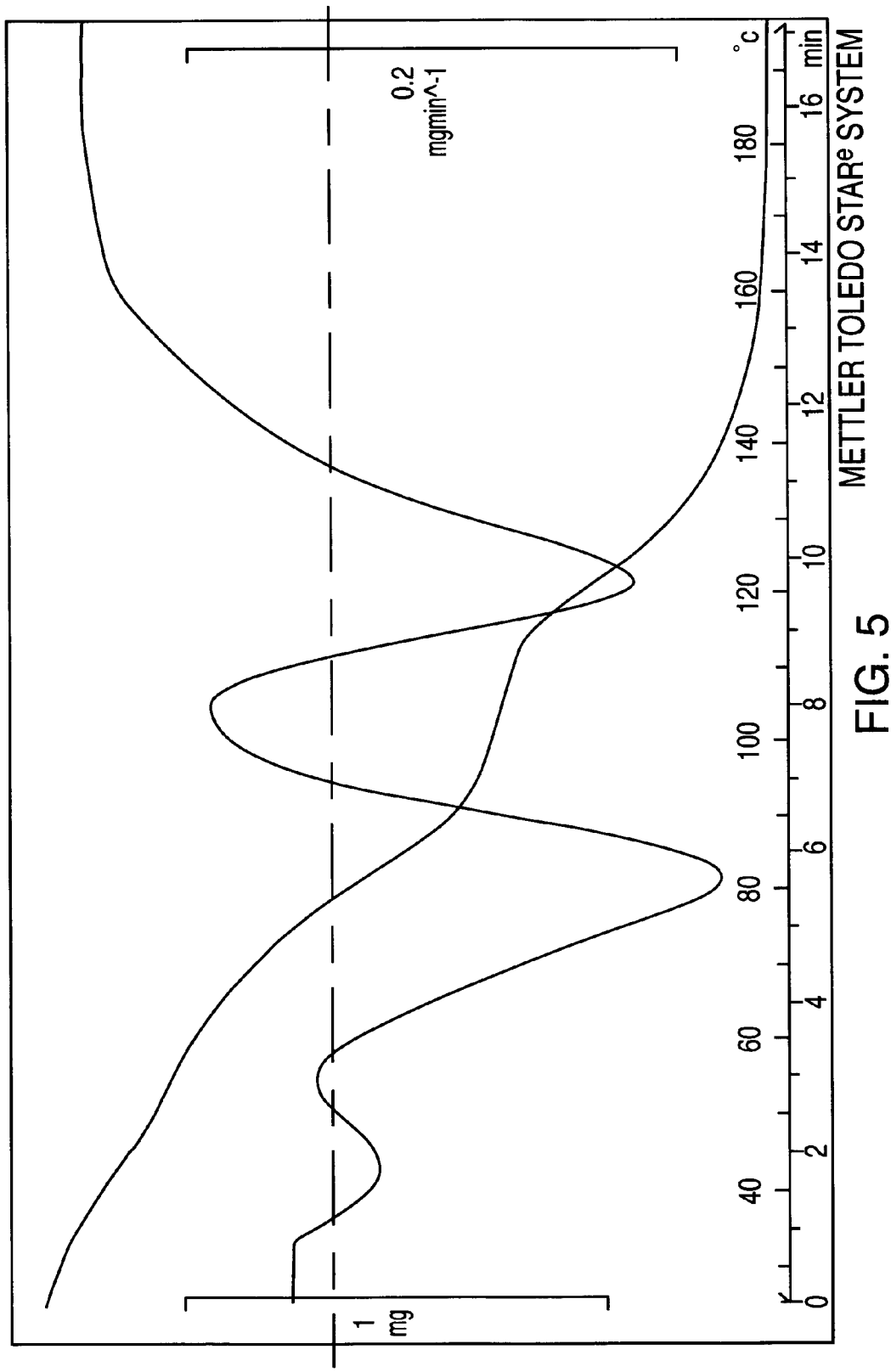
FIG. 5 is a thermogravimetric analysis (TGA) and calculated first derivative curve of losartan potassium Form III.

In another embodiment, this invention provides novel losartan potassium in a crystalline form that is a hydrate. The character of the new form is confirmed by PXRD patterns and TGA obtained from a sample thereof which are provided as FIGS. 4 and 5. The PXRD pattern shows characteristic peaks at about 5.7, 8.9, 13.3, 17.5, 20.0, and 21.1±0.2 degrees 2θ. Further, TGA confirms the presence of water of hydration in the sample. The total LOD (loss on drying) by TGA is between about 12 to 16 weight percent, and more specifically about 14 weight percent. The calculated first derivative curve shows three weight loss steps during heating by TGA. Losartan potassium in a crystalline form that is a hydrate in particular, a tetrahydrate, is designated Form III.

In another embodiment, the present invention provides a process for preparing losartan potassium in a crystalline form that is a hydrate, including the step of exposing amorphous losartan potassium or losartan potassium Form I to an atmosphere having high relative humidity (RH), preferably greater than about 60% RH, preferably greater than about 70% RH, and most preferably greater than about 80% RH. The crystalline form that is a hydrate has at least one characteristic of Form III. Preferably, the exposing step involves spreading a thin layer of losartan potassium particles on a surface, and, for example, placing the losartan potassium in a controlled humidity cell. A sample can be placed in the cell preferably for a period of time of at least about a day, and more preferably up to about five days.

Figure 6:
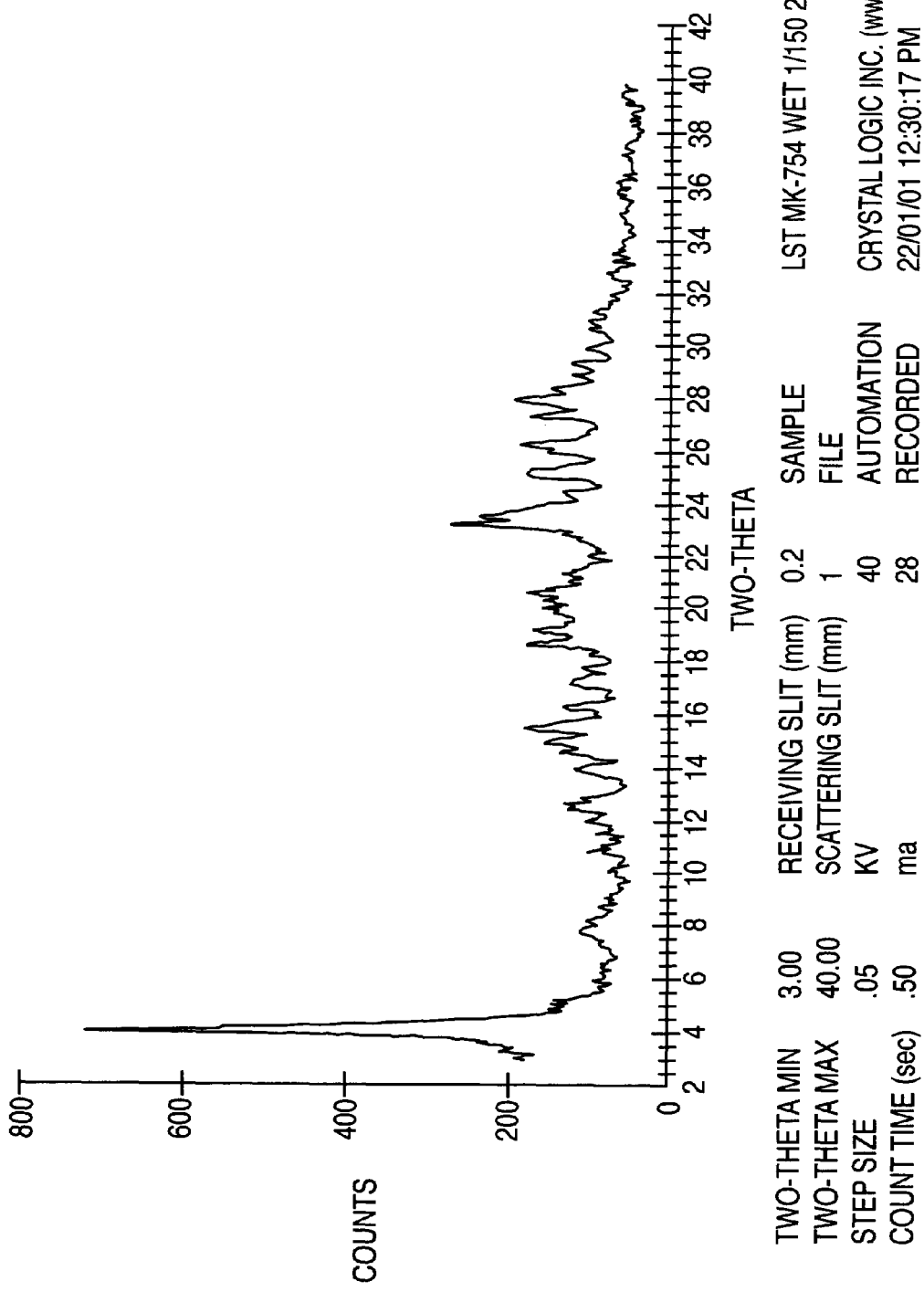
FIG. 6 is a PXRD pattern for losartan potassium Form IV.
Figure 7:
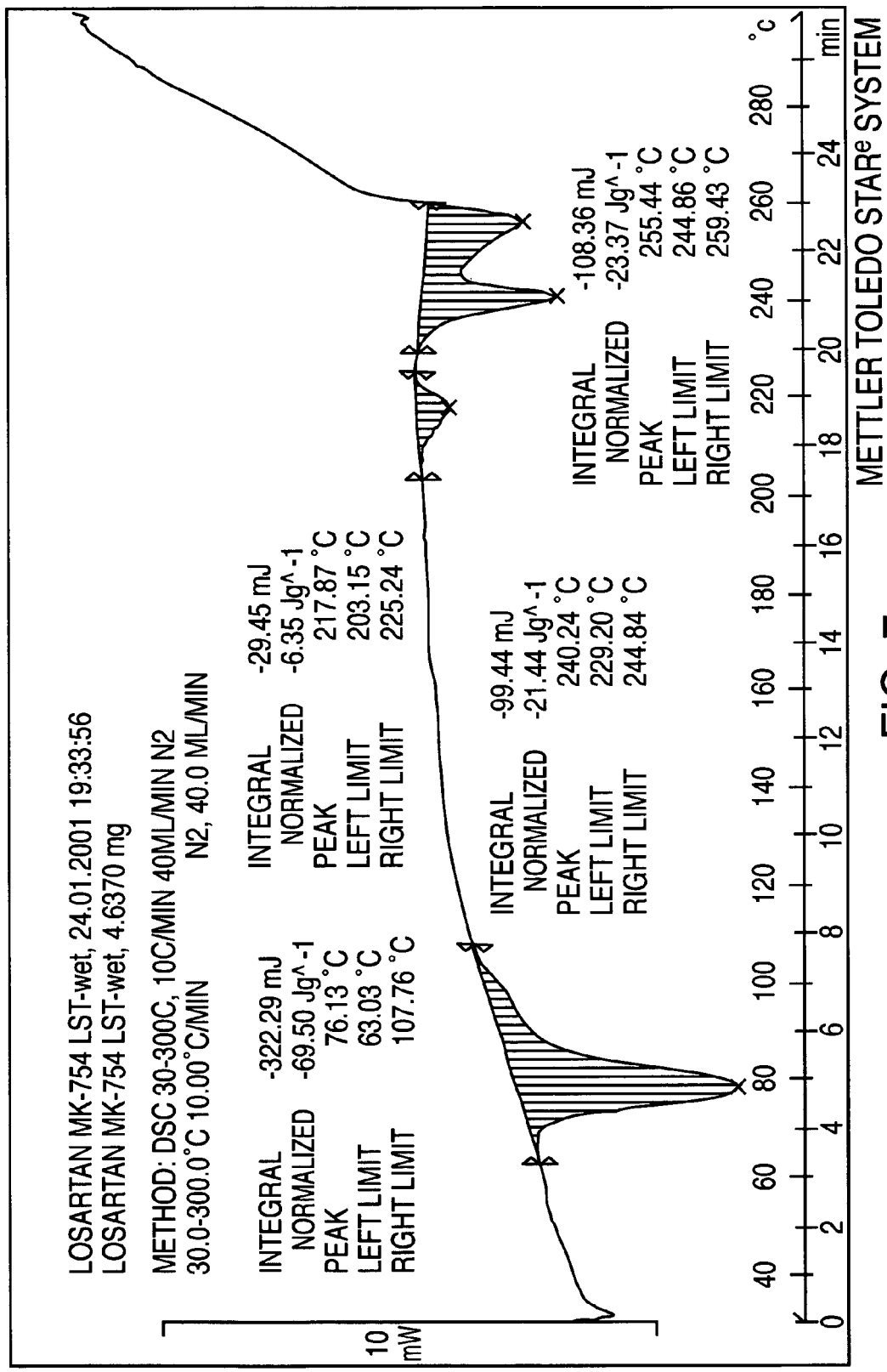
FIG. 7 is a DSC thermogram for losartan potassium Form IV.

In another embodiment, this invention provides novel losartan potassium Form IV and solvates thereof. The character and purity of the new form is confirmed by PXRD patterns obtained from a sample thereof which is provided as FIG. 6. The PXRD pattern shows characteristic peaks at about 4.3, 15.6, and 23.4±0.2 degrees 2θ. The DSC thermogram of losartan potassium Form IV shows four endotherms at about 78° C., 218° C., 240° C., and 255° C. Preferably, the solvate is an ethanolate.

In another aspect, the present invention relates to a process for preparing losartan potassium and solvates thereof having at least one characteristic of Form IV, including the steps of providing a solution of losartan potassium in a solvent to form a solution, the solvent being characterized as having a boiling point of from about 65° C. to about 135° C. or below (e.g. ethanol), adding methylene chloride to the solution whereby a suspension is formed, and isolating losartan potassium Form IV therefrom. The process further includes the steps of reducing the temperature of the suspension and maintaining the suspension at reduced temperature for a holding time. Losartan potassium Form IV and solvates thereof, preferably the ethanolate, can be separated from the mixture by conventional means such as filtration and can be optionally dried at ambient or elevated temperatures.

Preferably the solvent has a boiling point of about 135° C. or less, and more preferably about 120° C. or less. Preferred solvents are alcohols, more preferably lower alcohols having from 1 to 6 carbon atoms in any isomeric configuration, the most preferred solvent being ethanol. The losartan potassium starting material can be dissolved in the solvent wherein heat is used to effect dissolution. Preferably the starting material is dissolved at the reflux temperature of the solvent.

After forming a suspension, preferably the temperature of the suspension is reduced to about 2-3° C. and the suspension is preferably maintained at this temperature for a holding time of about 1 to about 3 hours.

Figure 8:
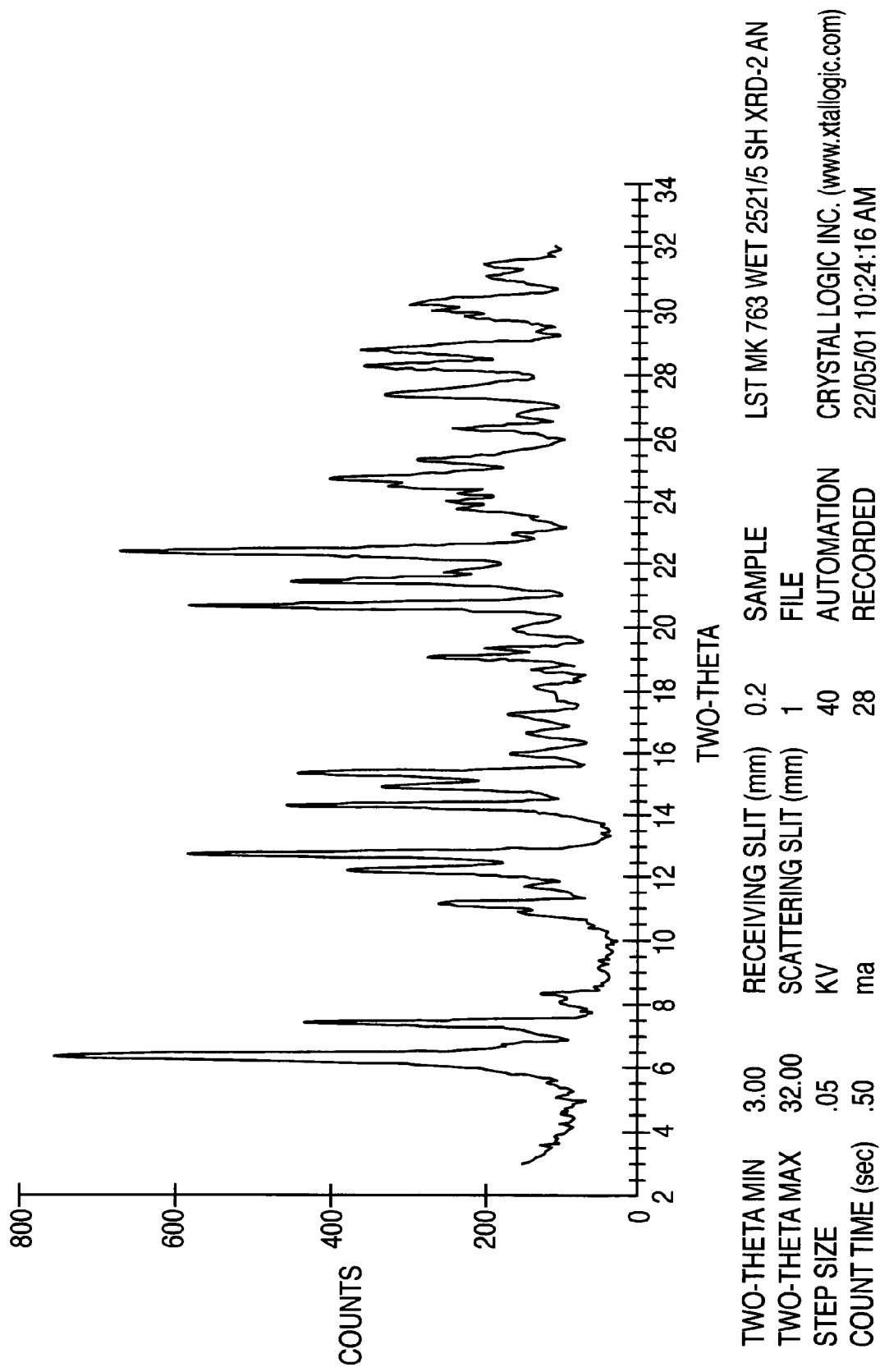
FIG. 8 is a PXRD pattern for losartan potassium Form V.

In another embodiment, this invention provides novel losartan potassium Form V and solvates thereof. The character and purity of the new form is confirmed by PXRD patterns obtained from a sample thereof which is provided as FIG. 8. The PXRD pattern shows characteristic peaks at about 6.4, 12.2, 20.7, 21.5 and 22.5±0.2 degrees 2θ. Preferably, the solvate is an ethanolate.

In another embodiment, this invention provides a process for preparing losartan potassium and solvates thereof having at least one characteristic of Form V, including the steps of providing a solution of losartan potassium in a solvent to form a solution, the solvent being characterized as having a boiling point of about 135° C. or below (e.g. ethanol), adding hexane to form a mixture, and isolating losartan potassium Form V and solvates thereof. The process further includes the steps of reducing the temperature of the mixture and maintaining the mixture at reduced temperature for a holding time. Losartan potassium Form V and solvates thereof, preferably the ethanolate, can be separated from the mixture by conventional means such as filtration and can be optionally dried at ambient or elevate temperatures.

Preferably the solvent has a boiling point of about 135° C. or below, and more preferably about 120° C. or below. Preferred solvents are alcohols, more preferably lower alcohols having from 1 to 6 carbon atoms in any isomeric configuration, the most preferred solvent being ethanol. The losartan potassium starting material can be dissolved in the solvent wherein heat is used to effect dissolution. Preferably the starting material is dissolved at the reflux temperature of the solvent.

After forming a mixture, preferably the temperature of the mixture is reduced to about 2-3° C. and is preferably maintained at this temperature for a holding time of about 1 to about 3 hours.

In another embodiment, this invention provides a novel process for producing losartan potassium Form II, including the steps of providing a solution of losartan potassium in a solvent to form a solution, the solvent being characterized by its capacity to solubilize losartan potassium at room temperature at a concentration up to at least about 0.1 gram per milliliter of solvent and as having a boiling point of about 135° C. or below (e.g. ethanol), adding the solution to xylene to form a mixture, evaporating the solvent from the mixture, and isolating losartan potassium Form II therefrom. Losartan potassium Form II can be separated from the mixture by conventional means such as filtration and can be optionally dried at ambient or elevated temperatures.

Figure 9:
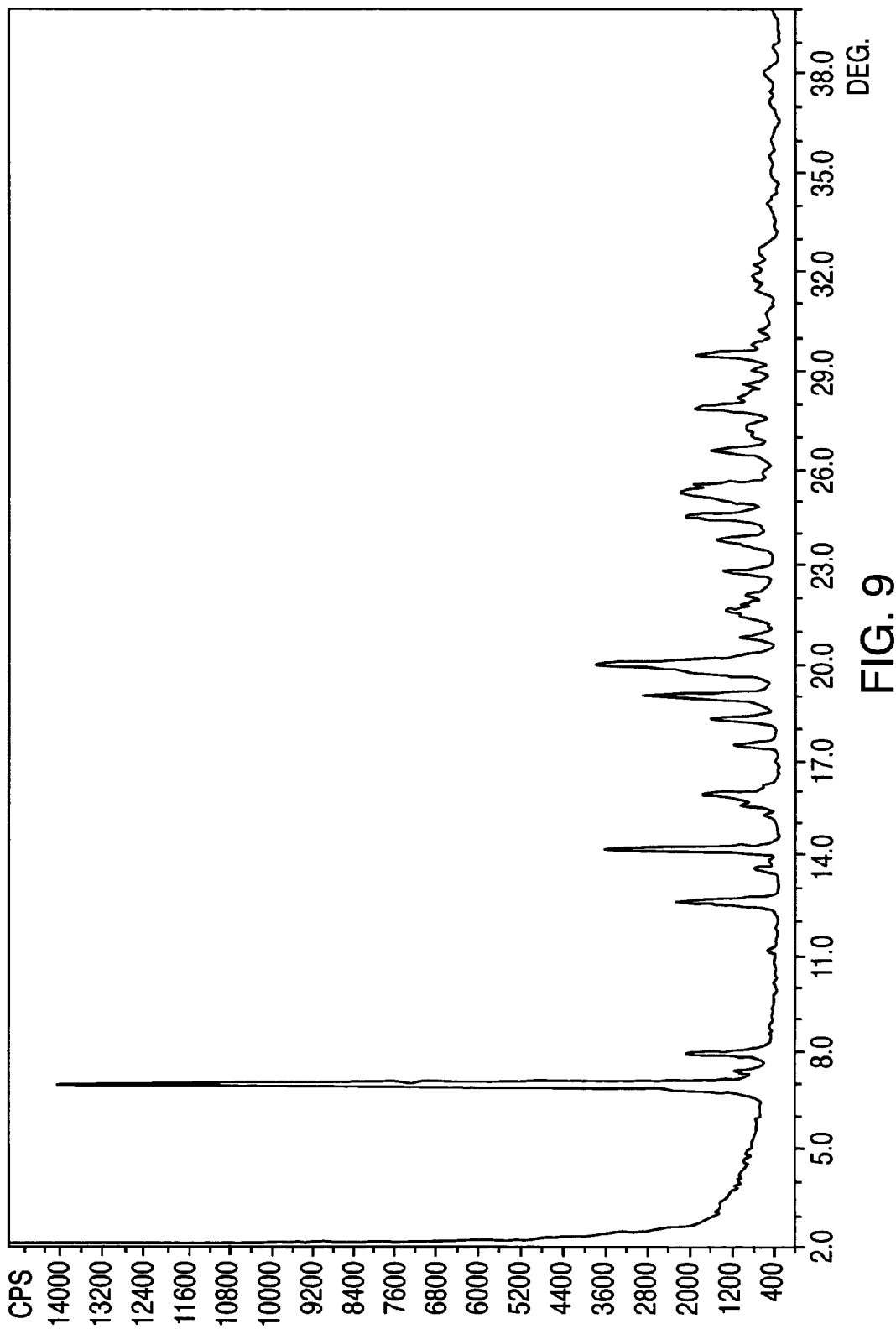
FIG. 9 is a PXRD pattern for Form II losartan potassium obtained by crystallization from hot xylene.

The spectroscopic characteristics of losartan potassium Form II that enable its identification and distinction from Form I and amorphous losartan potassium are set forth in U.S. Pat No. 5,608,075. FIG. 9 depicts a powder X-ray diffraction pattern of losartan potassium Form II prepared by the process of this invention.

According to the '075 patent, losartan potassium Forms I and II are enantiotropic, i.e., one form is more stable in a lower temperature range, while the other is more stable at a higher temperature. In the '075 patent, Form I was transformed into Form II by heating crystals of Form I in a differential scanning calorimeter. The transition began to occur at about 229° C. and can be seen as a minor broad endotherm that appears to span about 20° C. in the DSC thermogram of Form I, which is provided as FIG. 1(a) of the '075 patent. The '075 patent does not report whether the thermal transition is reversible at a kinetically significant rate. Rather, the reverse transition is reported to be facilitated by recrystallization from certain solvents.

We have discovered that Form II is accessible by recrystallization from xylene (the term xylene is meant to encompass all isomers of dimethyl benzene and mixtures thereof). Losartan potassium, either crystalline or amorphous, has low solubility in xylene. Therefore, it was necessary to develop a procedure whereby the recrystallization can be performed without consuming an impractical quantity of xylene or resorting to temperatures above 200° C. According to this preferred procedure, losartan potassium other than chemically pure crystalline Form II, as well as any mixture of Form II with losartan potassium, can be used as the starting material. To obtain Form II in high chemical purity the starting material should also be chemically pure. Whether the starting material is pure Form I, impure Form II or pure amorphous losartan potassium or a mixture thereof, however, is not critical to the process since the starting material is dissolved.

The starting material is dissolved in a solvent in which it is appreciably soluble. The phrase "appreciably soluble" means that amorphous losartan potassium is soluble to the extent of at least 0.1 g/ml at 25° C. Form I can be more or less soluble. The solvent also has a boiling point of about 135° C. or less, more preferably about 120° C. or less. Preferred solvents are alcohols, more preferably lower alcohols having from 1 to 6 carbon atoms in any isomeric configuration, the most preferred solvent being ethanol.

The concentration of losartan potassium in the solvent preferably approaches the saturation point of the solvent. A concentration of 0.2 grams of losartan potassium to ethanol is suitable when ethanol is used.

The concentrated solution of losartan potassium is added to xylene that is maintained at elevated temperature, at or above the boiling point of the solvent. Preferably, before the addition, the xylene has been brought to reflux, or nearly so, in a vessel with a pot temperature of from about 135° C. to about 150° C. For safety and economy, the vessel should be equipped with a condenser suitable for capture and return of a major portion of the xylene vapors. Addition of the concentrated solution is preferably performed rapidly as a single addition. The condenser should be of such a design and its temperature so regulated that the condenser will allow escape of solvent vapors (e.g. ethanol) while condensing a major portion of the xylene vapors. The evaporation of the solvent can be monitored by a temperature sensor provided within the vessel. After the addition, a temperature drop can be noted along with a gradual increase over time. If no heating adjustments are made during the process, return of the pot temperature to the temperature it was at before the addition will indicate that the solvent has substantially completely evaporated through the condenser. In addition, a mixture that remains cloudy or the presence of precipitate whose volume does not appear to change over time also signals that evaporation of the solvent is nearly complete. Thereafter, the mixture is cooled or allowed to cool and losartan potassium Form II is collected by any conventional means, such as by filtering.

It will be appreciated by those in the art that one advantage of this process for transforming losartan potassium Form I into Form II is that it enables the transformation at a much lower temperature than by the known method, some 80° C. lower. The potential for partial chemical decomposition that accompanies the use of higher temperatures is thereby avoided (rapid decomposition of losartan potassium occurs at 269° C.). Further, depending upon the efficiency of the condenser, the purity of the starting losartan and the method by which the xylene and Form II are separated, the xylene can be recycled, further improving the economics of the process.

In another embodiment, this invention provides a process for preparing crystalline losartan potassium Form I, including the steps of providing a solution of losartan potassium in a first solvent to form a solution, the first solvent being characterized as having a boiling point of about 135° C. or below (e.g. ethanol and isopropyl alcohol), reducing the temperature of the solution, optionally adding a second solvent selected from the group consisting of ethyl acetate, toluene, acetone, methyl ethyl ketone, methylene chloride, acetonitrile, dimethyl carbonate, and hexane to form a mixture, and isolating losartan potassium Form I therefrom. Losartan potassium Form I can be separated from the mixture by conventional means such as filtration and can be optionally dried at ambient or elevated temperature.

Preferably the first solvent has a boiling point of about 135° C. or less, and more preferably about 120° C. or less. Preferred solvents are alcohols, more preferably lower alcohols having from 1 to 6 carbon atoms in any isomeric configuration, the most preferred solvents being ethanol and isopropanol.

Preferably the temperature of the solution is reduced to about 25° C. or less, more preferably about 10° C., and most preferred between about 2-3° C. If a second solvent is used to form a mixture, preferably the mixture is maintained at a reduced temperature for about 1 to about 3 hours.

In another embodiment, the present invention provides a process for preparing crystalline losartan potassium Form I including the step of heating losartan potassium Form III. Preferably losartan potassium Form III is heated to a temperature of at least about 50° C., and more preferably about 100° C. for a holding time sufficient to effect transformation. A holding time of from about 15 minutes to about 1 hour is typically sufficient.

Solid amorphous losartan potassium, losartan potassium Form III, and losartan potassium Forms IV and V and solvates thereof can be milled into a powder. The powder can be used in a pharmaceutical product or physically modified such as by granulation to produce larger granules. Solid amorphous losartan potassium, losartan potassium Form III, and losartan potassium Forms IV and V and solvates thereof can also be used to prepare a liquid pharmaceutical product by dissolving or dispersing it in a liquid medium such as water, glycerin, vegetable oil and the like as discussed in greater detail below.

Solid amorphous losartan potassium, losartan potassium Form III, and losartan potassium Forms IV and V and solvates thereof are useful for treating patients with hypertension and for producing a hypotensive effect in mammals, including human patients. Solid amorphous losartan potassium, losartan potassium Form III, and losartan potassium Forms IV and V and solvates thereof can be formulated into a variety of compositions for administration to humans and mammals.

Pharmaceutical compositions of the present invention contain solid amorphous losartan potassium, losartan potassium Form III, and losartan potassium Forms IV and V and solvates thereof, and Forms IV and V and solvates thereof, optionally in mixture with other crystalline forms and/or other active ingredients such as hydrochlorothiazide. In addition to the active ingredient(s), the pharmaceutical compositions of the present invention can contain one or more excipients. Excipients are added to the composition for a variety of purposes.

Diluents increase the bulk of a solid pharmaceutical composition and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flow properties of non-compacted solid composition and improve the accuracy of dosing. Excipients that can function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product form the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, solid amorphous losartan potassium, losartan potassium Form III, and losartan potassium Forms IV and V and solvates thereof and any other solid excipients are dissolved or suspended in a liquid carrier such as water, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain a viscosity-enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at levels safe for ingestion to improve storage stability.

A liquid composition according to the present invention can also contain a buffer such as guconic acid, lactic acid, citric acid or acetic acid, sodium guconate, sodium lactate, sodium citrate or sodium acetate.

Selection of excipients and the amounts to use can be readily determined by the formulation scientist based upon experience and consideration of standard procedures and reference works in the field.

The solid compositions of the present invention include powders, granulates, aggregates and compacted compositions.

Solid amorphous losartan potassium, losartan potassium Form III, and losartan potassium Forms IV and V and solvates thereof can be administered for treatment of hypertension by any means that delivers the active pharmaceutical ingredient(s) to the site of the body where competitive inhibition of an $AT_1$ receptor exerts a therapeutic effect on the patient. For example, administration can be oral, buccal, parenteral (including subcutaneous, intramuscular, and intravenous) rectal, inhalant and ophthalmic. Although the most suitable route in any given case will depend on the nature and severity of the condition being treated, the most preferred route of the present invention is oral. Solid amorphous losartan potassium, losartan potassium Form III, and losartan potassium Forms IV and V and solvates thereof can be conveniently administered to a patient in oral unit dosage form and prepared by any of the methods well-known in the pharmaceutical arts. Dosage forms include solid dosage forms like tablets, powders, capsules, sachets, troches and lozenges as well as liquid syrups, suspensions and elixirs.

The active ingredient(s) and excipients can be formulated into compositions and dosage forms according to methods known in the art.

A composition for tableting or capsule filing can be prepared by wet granulation. In wet granulation some or all of the active ingredients and excipients in powder form are blended and then further mixed in the presence of a liquid, typically water, that causes the powders to clump up into granules. The granulate is screened and/or milled, dried and then screened and/or milled to the desired particle size. The granulate can then be tableted or other excipients can be added prior to tableting such as a glidant and/or lubricant.

A tableting composition can be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

Yet more particularly, a tablet can, for example, be formulated by blending 100 mg spray dried lactose, 50 mg of amorphous losartan potassium, losartan potassium Form III, and losartan potassium Forms IV and V and solvates thereof, 5 mg of magnesium stearate and directly compressing the composition in a tablet machine.

A capsule can, for example, be prepared by filling half of a gelatin capsule with the above tablet composition and capping it with the other half of the gelatin capsule.

A simple parenteral solution for injection can, for example, be prepared by combining 1.5% amorphous losartan potassium, losartan potassium Form III, and losartan potassium Forms IV and V and solvates thereof, sterile 10% propylene glycol and 88.5% sterile water and sealing the composition in a sterile vial under sterile conditions.

Capsules, tablets and lozenges and other unit dosage forms preferably contain a dosage level of about 10 mg to about 100 mg, more preferably from about 25 mg to about 50 mg of losartan potassium.

Having thus described the present invention with reference to certain preferred embodiments, the processes for producing amorphous losartan potassium, losartan potassium Form III, losartan potassium Form IV and solvates thereof, losartan potassium Form V and solvates thereof, losartan potassium Form II, and losartan potassium Form I of the present invention are further illustrated by the examples that follow. These examples are provided for illustrative purposes only and are not intended to limit in any way the invention, which is defined by the claims following the examples.

EXAMPLES

General

The powder X-ray diffraction patterns were obtained by methods known in the art using a SCINTAG powder X-ray diffractometer model X'TRA, variable goniometer, equipped with a solid-state detector. Copper radiation of $\lambda=1.5418$ Å was used. Scanning parameters: measurement range: 2-40 degrees 2θ; continuous scan; rate: 3 degrees per minute.

The thermogravimetric curves were obtained by methods known in the art using a Mettler TGA TG50. The weight of the samples was about 1 mg. The temperature range was from about 25° C. to at least 190° C. at the rate of 10° C./min. Samples were purged with nitrogen gas at a flow rate of 40 ml/min.

The differential scanning calorimeter thermograms were obtained by methods known in the art using a DSC Mettler Toledo Star$^e$ system. The weight of the samples was about 4.6 mg. The temperature range of scans was from about 30° C. to about 250° C. at a rate of 10° C./min. Samples were purged with nitrogen gas at a flow rate of 40 mL/min.

Example 1

Amorphous Losartan Potassium

Losartan potassium (1 g) was stirred in water (2 ml) in a round bottom flask until it dissolved. The solution was then transferred to a heavy walled lyophilization tray. The lyophilizer was cooled to below freezing to about −5° C. The lyophilizer was evacuated and maintained under about 0.01 mm Hg vacuum for about 2 hours. The residue was submitted for powder X-ray analysis, which produced a featureless diffractogram with a broad peak centered at about 22 degree 2θ (FIG. 1).

Example 2

Amorphous Losartan Potassium

Losartan potassium salt (10 g) was dissolved in methanol (100 ml) to obtain a clear solution. The solvent was evaporated under vacuum (~100 mm Hg) at about 20 to about 50° C. Drying was continued under vacuum at about 60° C. to about 80° C. for about one hour. Similar to Example 1 above, the powder X-ray diffractogram of the solid (FIG. 2), having a broad peak centered at about 22 degrees 2θ, showed that the resulting substance was in amorphous form.

Example 3

Losartan Potassium Form III

Losartan potassium Form I (200 mg) was spread as a thin layer in a small plastic dish and placed in a controlled humidity cell having a relative humidity of about 80-100% for five days.

Example 4

Losartan Potassium Form III

Losartan potassium amorphous (200 mg) was spread as a thin layer in a small plastic dish and placed in a controlled humidity cell having a relative humidity of about 80-100% for five days.

Example 5

Losartan Potassium Form IV

Losartan potassium (5 g) was dissolved in refluxing ethanol (5 ml) at a pot temperature of about 90° C., and then cooled to a temperature of about 50° C. Methylene chloride (75 ml) was slowly added over one hour. The mixture was then cooled to about 2-3° C. for a period of about 3 hours. The product was then filtered and dried at 50° C. under vacuum (~0.1 mm Hg) to yield losartan potassium Form IV.

Example 6

Losartan Potassium Form V

Losartan potassium (5 g) was dissolved in refluxing ethanol (5.5 ml) at a pot temperature of about 90° C. Hexane (25 ml) was slowly added over one hour, while the mixture was cooled to room temperature. The mixture was then gradually cooled to about 2-3° C. and then maintained at this temperature for a period of about 3 hours. The product was then filtered and dried at 50° C. under vacuum (~0.1 mm Hg) to yield losartan potassium Form V.

Example 7

Losartan Potassium Form II

A concentrated solution of losartan potassium (1 g) in ethanol (5 ml) was poured rapidly into vigorously refluxing xylene (30 ml) at a pot temperature of 145° C. The mixture was maintained at 145° C. as ethanol was distilled off. After a while, losartan potassium came out of solution in the refluxing mixture. The mixture was cooled and filtered. The collected solid was dried under reduced pressure at 40° C. for 2 h. The powder X-ray diffractogram of the solid (FIG. 4) shows that it was mainly losartan potassium Form II.

Example 8

Losartan Potassium Form I

In a three-necked round bottom flask (100 ml) that was equipped with a condenser and thermometer, losartan potassium (5 g) was dissolved in ethanol (8.5 ml) at room temperature. The solution was then cooled to about 2-3° C. and ethyl acetate (75 ml) was slowly added to the solution over about 45 minutes. The mixture was stirred at this temperature for about 2 hours and was then filtered and dried at about 40° C. overnight under vacuum (~0.1 mm Hg) to yield losartan potassium Form I.

Example 9

Losartan Potassium Form I

In a three-necked round bottom flask (100 ml) that was equipped with a condenser and thermometer, losartan potassium (5 g) was dissolved in ethanol (7.5 ml) at room temperature. The solution was then cooled to about 2-3° C. and toluene (80 ml) was dropped into the solution within about 45 minutes. The mixture was stirred at this temperature for about 2 hours and was then filtered and dried at about 40° C. overnight under vacuum (~0.1 mm Hg) to yield losartan potassium Form I.

Example 10

Losartan Potassium Form I

In a three-necked round bottom flask (100 ml) that was equipped with a condenser and thermometer, losartan potassium (5 g) was dissolved in boiling ethanol (6 ml). The solution was then cooled gradually to room temperature and then to about 2-3° C. and acetone (100 ml) was dropped into within about 45 minutes. The mixture was stirred at this temperature for about 2 hours and was then filtered and dried at about 40° C. overnight under vacuum (~0.1 mm Hg) to yield losartan potassium Form I.

Example 11

Losartan Potassium Form I

In a round bottom flask (50 ml), losartan potassium (5 g) was dissolved in boiling ethanol potassium (5.5 ml). The solution was then cooled gradually to room temperature and then to about 2-3° C. within about 45 minutes. The mixture was stirred at this temperature for about 2 hours and was then filtered and dried at about 40° C. overnight under vacuum (~0.1 mm Hg) to yield losartan potassium Form I.

Example 12

Losartan Potassium Form I

In a three-necked round bottom flask (100 ml) that was equipped with a condenser and thermometer, losartan potassium (5 g) was dissolved in boiling ethanol (5.5 ml). The solution was then cooled gradually to room temperature and then to about 2-3° C. and methylethyl ketone (50 ml) was dropped into within about 45 minutes. The mixture was stirred at this temperature for about 2 hours and was then filtered and dried at about 40° C. overnight under vacuum (~0.1 mm Hg) to yield losartan potassium Form I.

Example 13

Losartan Potassium Form I

In a three-necked round bottom flask (100 ml) that was equipped with a condenser and thermometer, losartan potassium (5 g) was dissolved in boiling ethanol (5 ml). The solution was then cooled gradually to room temperature and then to about 2-3° C. and methylene chloride (75 ml) was dropped into within about 45 minutes. The mixture was stirred at this temperature for about 2 hours and was then filtered and dried at about 40° C. overnight under vacuum (~0.1 mm Hg) to yield losartan potassium Form I.

Example 14

Losartan Potassium Form I

In a three-necked round bottom flask (100 ml) that was equipped with a condenser and thermometer, losartan potassium (5 g) was dissolved in boiling ethanol (5 ml). The solution was then cooled gradually to room temperature and then to about 2-3° C. and acetonitrile (50 ml) was dropped into within about 45 minutes. The mixture was stirred at this temperature for about 2 hours and was then filtered and dried at about 40° C. overnight under vacuum (~0.1 mm Hg) to yield losartan potassium Form I.

Example 15

Losartan Potassium Form I

In a three-necked round bottom flask (100 ml) that was equipped with a condenser and thermometer, losartan potassium (5 g) was dissolved in boiling ethanol (5 ml). The solution was then cooled gradually to room temperature and then to about 2-3° C. and dimethyl carbonate (25 ml) was dropped into within about 45 minutes. The mixture was stirred at this temperature for about 2 hours and was then filtered and dried at about 40° C. over night under vacuum (~0.1 mm Hg) to yield losartan potassium Form I.

Example 16

Losartan Potassium Form I

In a three-necked round bottom flask (100 ml) that was equipped with a condenser and thermometer, losartan potassium (5 g) was dissolved in boiling ethanol (5.5 ml). The solution was then cooled gradually to room temperature and then to about 2-3° C. and hexane (25 ml) was dropped into within about 45 minutes. The mixture was stirred at this temperature for about 2 hours and was then filtered and dried at about 40° C. overnight under vacuum (~0.1 mm Hg) to yield losartan potassium Form I.

Example 17

Losartan Potassium Form I

In a three-necked round bottom flask (100 ml) that was equipped with a condenser and thermometer, losartan potassium (3 g) was dissolved in boiling isopropyl alcohol (30 ml). The solution was then cooled gradually to room temperature and then to about 2-3° C. The mixture was stirred at this temperature for about 2 hours and was then filtered and dried at about 40° C. overnight under vacuum (~0.1 mm Hg) to yield losartan potassium Form I.

Example 18

Losartan Potassium Form I

In a three-necked round bottom flask (100 ml) that was equipped with a condenser and thermometer, losartan potassium (5 g) was dissolved in boiling isopropyl alcohol (27 ml). The solution was then cooled gradually to room temperature and then to about 2-3° C. and toluene (100 ml) was dropped into within about 45 minutes. The mixture was stirred at this temperature for about 2 hours and was then filtered and dried at about 40° C. overnight under vacuum (~0.1 mm Hg) to yield losartan potassium Form I.

Example 19

Losartan Potassium Form I

In a three-necked round bottom flask (100 ml) that was equipped with a condenser and thermometer, losartan potassium (5 g) was dissolved in boiling isopropyl alcohol (27 ml). The solution was then cooled gradually to room temperature and then to about 2-3° C. and ethyl acetate (100 ml) was dropped into within about 45 minutes. The mixture was stirred at this temperature for about 2 hours and was then filtered and dried at about 40° C. overnight under vacuum (~0.1 mm Hg) to yield losartan potassium Form I.

Example 20

Losartan Potassium Form I

In a three-necked round bottom flask (100 ml) that was equipped with a condenser and thermometer, losartan potassium (5 g) was dissolved in boiling isopropyl alcohol (27 ml). The solution was then cooled gradually to room temperature and then to about 2-3° C. and dimethyl carbonate (100 ml) was dropped into within about 45 minutes. The mixture was stirred at this temperature for about 2 hours and was then filtered and dried at about 40° C. overnight under vacuum (~0.1 mm Hg) to yield losartan potassium Form I.

Example 21

Losartan Potassium Form I

In a three-necked round bottom flask (100 ml) that was equipped with a condenser and thermometer, losartan potassium (5 g) was dissolved in boiling isopropyl alcohol (29 ml). The solution was then cooled gradually to room temperature and then to about 2-3° C. and methylene chloride (100 ml) was dropped into within about 45 minutes. The mixture was stirred at this temperature for about 2 hours and was then filtered and dried at 40° C. overnight under vacuum (~0.1 mm Hg) to yield losartan potassium Form I.

Example 22

Losartan Potassium Form I

In a three-necked round bottom flask (100 ml) that was equipped with a condenser and thermometer, losartan potassium (5 g) was dissolved in boiling isopropyl alcohol (27 ml) at room temperature. The solution was then cooled gradually to room temperature and then to about 2-3° C. and hexane (100 ml) was dropped into within about 45 minutes. The mixture was stirred at this temperature for about 2 hours and was then filtered and dried at about 40° C. overnight under vacuum (~0.1 mm Hg) to yield losartan potassium Form I.

We claim:

1. A process for preparing losartan potassium Form I comprising the steps of:
   (a) providing a solution of losartan potassium in a first solvent to form a solution, the solvent being characterized as having a boiling point of about 135° C. or below, wherein the first solvent is non-aqueous,
   (b) reducing the temperature of the solution,
   (c) adding a second solvent selected from the group consisting of ethyl acetate, toluene, acetone, methylethyl ketone, methylene chloride, acetonitrile, dimethyl carbonate, and hexane to form a mixture after reducing the temperature of the first solvent whereby a precipitate is formed, and
   (d) isolating losartan potassium Form I characterized by an X-ray powder diffraction pattern having X-ray powder diffraction angles of: 7.24, 11.02, 14.16, 15.07, 18.46, 18.87, 26.53, 27.30 and 29.15.

2. The process of claim 1 wherein the temperature of the solvent is reduced to about 2-3° C. and the mixture is maintained at about 2-3° C. for about 1 to about 3 hours.

3. The process of claim 1 wherein a slurry results from reducing the temperature of the solution.

4. The process of claim 1 wherein the first solvent is a $C_1$-$C_6$ alcohol.

5. The process of claim 4 wherein the $C_1$-$C_6$ alcohol is ethanol or isopropanol.

6. A process for preparing losartan potassium Form I comprising the steps of:
   (a) providing a solution of losartan potassium in a first solvent to form a solution, the solvent being characterized as having a boiling point of about 135° C. or below, wherein the concentration of losartan potassium in the solution is in the range of 0.1 g/ml to 1.0 g/ml,
   (b) reducing the temperature of the solution,
   (c) adding a second solvent selected from the group consisting of ethyl acetate, toluene, acetone, methylethyl ketone, methylene chloride, acetonitrile, dimethyl carbonate, and hexane to form a mixture after reducing the temperature of the first solvent whereby a precipitate is formed, and
   (d) isolating losartan potassium Form I characterized by an X-ray powder diffraction pattern having X-ray powder diffraction angles of: 7.24, 11.02, 14.16, 15.07, 18.46, 18.87, 26.53, 27.30 and 29.15.

7. The process of claim 6 wherein the temperature of the solvent is reduced to about 2-3° C. and the mixture is maintained at about 2-3° C. for about 1 to about 3 hours.

8. The process of claim 6 wherein a slurry results from reducing the temperature of the solution.

9. The process of claim 6 wherein the first solvent is a $C_1$-$C_6$ alcohol.

10. The process of claim 9 wherein the $C_1$-$C_6$ alcohol is ethanol or isopropanol.

* * * * *